US012569436B1

(12) United States Patent　　(10) Patent No.:　US 12,569,436 B1
Sun　　(45) Date of Patent:　Mar. 10, 2026

(54) SELF-REGULATING PHOTO-CURABLE COOLING HYDROGEL AND PREPARATION METHOD AND APPLICATION THEREOF

(71) Applicant: Zhejiang Haiya Commodity Co., Ltd., Ningbo (CN)

(72) Inventor: Yujie Sun, Ningbo (CN)

( * ) Notice: Subject to any disclaimer, the term of this patent is extended or adjusted under 35 U.S.C. 154(b) by 0 days.

(21) Appl. No.: 19/316,708

(22) Filed: Sep. 2, 2025

(51) Int. Cl.
| | |
|---|---|
| *A61K 9/06* | (2006.01) |
| *A61K 47/10* | (2017.01) |
| *A61K 47/14* | (2017.01) |
| *A61K 47/18* | (2017.01) |
| *A61K 47/26* | (2006.01) |

(52) U.S. Cl.
CPC ................ *A61K 9/06* (2013.01); *A61K 47/10* (2013.01); *A61K 47/14* (2013.01); *A61K 47/18* (2013.01); *A61K 47/26* (2013.01)

(58) Field of Classification Search
CPC ...................................................... A61K 9/06
See application file for complete search history.

(56)　　　References Cited

FOREIGN PATENT DOCUMENTS

CN　　　114456746 A * 5/2022 ............ C08F 289/00

* cited by examiner

*Primary Examiner* — Robert A Wax
*Assistant Examiner* — William Craigo

(57)　　　ABSTRACT

The invention belongs to the technical field of hydrogel materials, and specifically relates to a self-regulating photo-curable cooling hydrogel and a preparation method and an application thereof. The self-regulating photo-curable cooling hydrogel comprises the following raw materials in parts by weight: 10-17 parts of cooling matrix, 18-33 parts of acrylamide-$^{13}C_3$, 27-42 parts of glycerol, 5 parts of TPGDA (tripropylene glycol diacrylate), 0.05-0.15 parts of crosslinking agent, and 0.1-0.3 parts of photoinitiator. By constructing a synergistic system of antifreeze protein and konjac glucomannan skeleton, the gelation of an isotope-labeled monomer and the purpose of self-regulating cooling are achieved. It can be used for preparing drug-loaded gel dressings, cooling gel dressings, and in-situ injectable gel products. The photo-curable crosslinking technology facilitates the rapid molding of gel dressings and improves the stability of active ingredients.

8 Claims, 3 Drawing Sheets

SELF-REGULATING PHOTO-CURABLE COOLING HYDROGEL AND PREPARATION METHOD AND APPLICATION THEREOF

TECHNICAL FIELD

The invention belongs to the technical field of hydrogel materials, and specifically relates to a self-regulating photo-curable cooling hydrogel and a preparation method and an application thereof.

BACKGROUND ART

In biomedical and other application fields, cold hydrogel dressings have become key medical materials for alleviating traumatic burns and inhibiting inflammatory reactions due to their high water content, thermal buffering capacity, and flexible adhesion advantages. Conventional techniques integrate cooling agents such as menthol or borneol, enabling dressings to combine physical cooling with drug delivery, particularly suitable for exudative wounds like burns and acute soft tissue injuries. However, with increasing demands for precision medicine, inherent limitations of traditional cold hydrogels are becoming apparent. On the one hand, during the initial high-temperature, high-exudate stage of a wound, the sudden release of cooling agents causes intensified pain due to cold shock; conversely, during the repair phase when temperature subsides, premature cooling agent failure fails to suppress residual inflammatory heat. On the other hand, small molecule cooling agents and drugs easily migrate and leak into the wound, shortening the effective duration and potentially penetrating nascent epithelial tissue causing toxicity. In addition, functional component integration is difficult; temperature-responsive materials often exhibit poor compatibility with bioactive ingredients, while sustained-release processes like microencapsulation introduce synthetic polymer wall materials increasing biotoxicity risks and complex processes raising production costs. More critically, the molecular metabolic tracing function required for post-operative repair and disease research is often hampered by the structural instability of isotope-labeled molecules during thermal curing and the insufficient mechanical strength of UV-cured networks. These conflicts force current cold dressings to compromise between temperature self-adaptability, long-acting drug release, and biosafety, severely limiting their use in chronic wounds and precision medicine.

Therefore, there is an urgent need to develop a novel hydrogel dressing capable of providing long-lasting cooling, strong isotope stability, and good biocompatibility to overcome the technical limitations of current cooling gel materials.

SUMMARY OF THE INVENTION

To address the above issues, the invention provides a self-regulating photo-curable cooling hydrogel and a preparation method and an application thereof. Through a biomimetic strategy forming a cooling matrix with allosteric dissociation characteristics from antifreeze protein and hinokitiol, constructing a gel skeleton network, and optimizing an isotope-labeled monomer with a UV-curing system, precise crosslinking of a photosensitive network is achieved. This hydrogel can serve as a carrier dressing for drug delivery or body temperature regulation.

To achieve the above objective, the technical solution adopted by the invention is as follows.

The invention provides a self-regulating photo-curable cooling hydrogel, wherein the hydrogel comprises the following raw materials in parts by weight: 10-17 parts of cooling matrix, 18-33 parts of acrylamide-$^{13}C_3$, 27-42 parts of glycerol, 5 parts of TPGDA (tripropylene glycol diacrylate), 0.05-0.15 parts of crosslinking agent, and 0.1-0.3 parts of photoinitiator.

Further, the crosslinking agent is selected from any one of MBA (N,N'-methylenebisacrylamide), PEG400 (polyethylene glycol 400), and HAMA (methacrylated hyaluronic acid).

Further, the photoinitiator is selected from any one of TPO-L (ethyl (2,4,6-trimethylbenzoyl) phenylphosphinate) and Irgacure 2959 (2-hydroxy-4'-(2-hydroxyethoxy)-2-methylpropiophenone).

Further, the cooling matrix comprises the following raw materials: antifreeze protein, menthyl amide, konjac glucomannan, hinokitiol, NHS (N-hydroxysuccinimide), $CaCl_2$), and β-mannanase; the preparation method of the cooling matrix comprises the following steps: Further, the mass ratio of the antifreeze protein, menthyl amide, konjac glucomannan, hinokitiol, NHS, $CaCl_2$), and β-mannanase is 15:1:22.5:4.7:0.3:0.5:0.15.

The preparation method of the cooling matrix comprises the following steps:

S1: weighing konjac glucomannan and dissolving it in deionized water, adding β-mannanase and reacting for 30 minutes, then deactivating the enzyme at 90° C., subsequently adding hinokitiol and NHS, reacting at 50° C. under nitrogen atmosphere for 3 hours, followed by dialysis, to obtain a grafted solution;

S2: weighing antifreeze protein and dissolving it in deionized water to obtain an antifreeze protein solution; weighing menthyl amide and dissolving it in anhydrous ethanol, then adding it to the antifreeze protein solution at 4° C., 80 rpm, and a rate of 2 mL/min while stirring; after complete addition, continuing stirring for 4 hours, to obtain an inclusion solution;

S3: mixing the grafted solution and the inclusion solution, adding $CaCl_2$, and homogenizing at 12,000 rpm for 10 minutes, to obtain the cooling matrix.

The invention further provides a preparation method of the self-regulating photo-curable cooling hydrogel, and specifically comprises the following steps:

step 1: weighing 18-33 parts of acrylamide-$^{13}C_3$ and dissolving it in deionized water, adding 27-42 parts of glycerol, and stirring at 400 rpm for 15 minutes, to obtain an aqueous phase;

step 2: weighing 5 parts of TPGDA and 0.1-0.3 parts of the photoinitiator, mixing them under light-proof conditions, stirring at 200 rpm until clear, to obtain an oil phase; mixing the oil phase and the aqueous phase uniformly, then adding 10-17 parts of the cooling matrix and 0.05-0.15 parts of the crosslinking agent thereto, to obtain a pre-gel;

step 3: adjusting the pH of the pre-gel to 4.0-5.5 using a pH 4.0 citrate buffer, and drying in a 60° C. vacuum drying oven until the water content is 18-22%, to obtain the self-regulating photo-curable cooling hydrogel.

The invention further provides an application of the self-regulating photo-curable cooling hydrogel, wherein the above photo-curable cooling hydrogel is used for preparing drug-loaded gel dressings, cooling gel pads, cooling gel dressing bags, cooling gel injection products, and in-situ injectable gels.

Further, for the application of the self-regulating photo-curable cooling hydrogel in preparing a cooling gel pad, the specific preparation method is as follows: using an adsorption mold production method, taking a cleaned and dried mold with various pattern shapes, injecting the prepared cooling hydrogel therein, curing under 365 nm wavelength, 25 mW/cm² UV light irradiation for 60 seconds, performing compression molding, and processing a surface plastic film, to obtain the cooling gel pad.

Further, the cooling gel pad is applicable to sporting goods, office supplies, and automotive supplies.

Further, the cooling gel pad is usable for producing seat cushions, pet pads, yoga mats, mattresses, clothing, gloves, and headwear products.

Further, for the application of the self-regulating photo-curable cooling hydrogel in preparing a cooling gel dressing bag, the specific preparation method is as follows: filling the prepared cooling hydrogel into a well-sealed dressing bag, curing under 365 nm wavelength, 25 mW/cm² UV light irradiation for 60 seconds, to obtain the cooling gel dressing bag.

Further, for the application of the self-regulating photo-curable cooling hydrogel in preparing a cooling gel injection product, the specific preparation method is as follows: injecting the prepared cooling hydrogel into latex or sponge, curing under 365 nm wavelength, 25 mW/cm² UV light irradiation for 60 seconds to shape, to obtain the cooling gel injection product.

Further, the cooling gel injection product is usable for producing pillows and lumbar support products.

Further, for the application of the self-regulating photo-curable cooling hydrogel in preparing a drug-loaded gel dressing, the specific preparation method is as follows: dispersing a drug in a solvent to obtain a drug solution; uniformly mixing the drug solution, Tween 80, and the cooling hydrogel in a mass ratio of 1:0.02:15 to obtain a drug-loaded gel; uniformly coating the drug-loaded gel onto a mold containing a dressing backing, curing under 365 nm wavelength, 25 mW/cm² UV light irradiation for 60 seconds, and performing compression molding, to obtain the drug-loaded gel dressing.

Further, the drug is selected from any one of indomethacin, mupirocin, rhEGF (recombinant human epidermal growth factor), and lidocaine.

Further, for the application of the self-regulating photo-curable cooling hydrogel in preparing an in-situ injectable gel, the cooling hydrogel is injected into a lesion site and cured with 365 nm UV light, for in vivo metabolic tracing.

The beneficial effects of the invention are as follows.

The self-regulating photo-curable cooling hydrogel prepared by the invention, based on a cooling matrix and a ternary solvent system of water/glycerol/TPGDA, constructs a temperature-controlled photo-curable hydrogel. It achieves the combination of the isotope-labeled monomer acrylamide-$^{13}C_3$ with UV-curing technology, improving the mechanical properties of acrylamide-based hydrogels. The antifreeze protein, as a natural thermosensitive carrier, enables the regulated release of menthyl amide. The enzymatically hydrolyzed konjac glucomannan skeleton obtains optimized swelling-shrinkage characteristics through molecular chain modification. The mechanical stress generated under temperature triggering synergizes with the sustained release behavior of hinokitiol, achieving a balance between cooling intensity and duration, ensuring elastic recovery properties while enabling rapid curing. The stepwise preparation involving enzymatic hydrolysis-grafting-encapsulation preserves the active sites of biomacromolecules and achieves efficient loading of functional factors. The pH adjustment and vacuum drying processes balance deaeration efficiency with gel network integrity, providing new insights for the functional development of photo-curable hydrogels.

Furthermore, the self-regulating photo-curable cooling hydrogel prepared by the invention exhibits good cooling and temperature-control capabilities, biocompatibility, and mechanical properties, enhancing adaptability for patients with fever, high temperature, skin trauma, or inflammation. It is suitable for biomedical fields, particularly as a skin cooling dressing or a carrier hydrogel dressing for wound repair, antibacterial, anti-inflammatory, and analgesic drugs.

BRIEF DESCRIPTION OF ACCOMPANY DRAWINGS

SPECIFIC EMBODIMENT OF THE INVENTION

Figure 1:
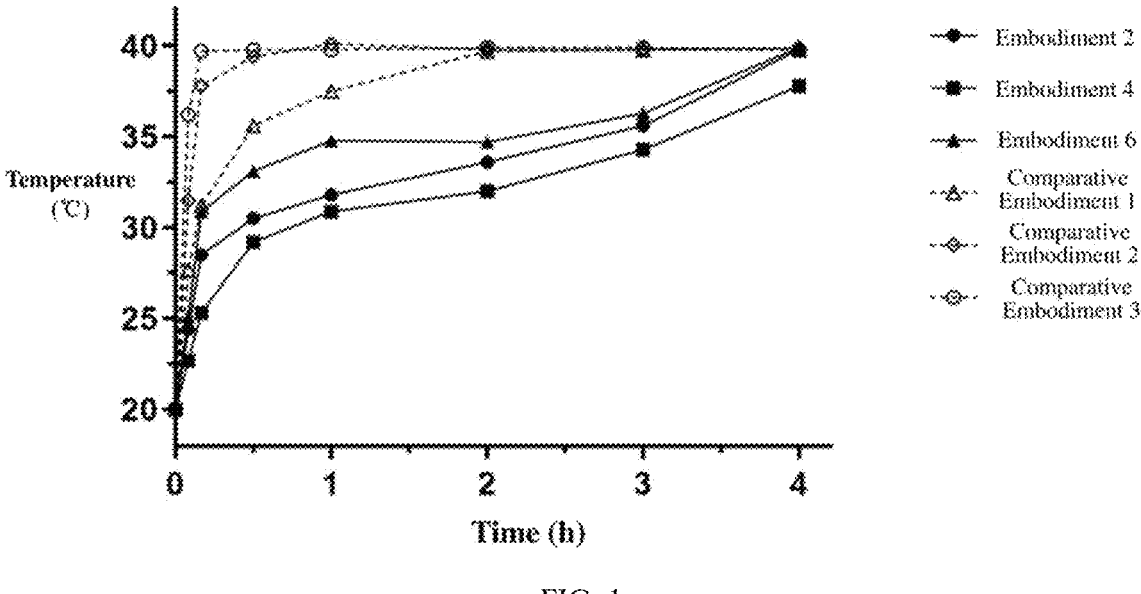
FIG. 1 shows the temperature-time change curves of the cooling hydrogels after photo-curing prepared in Embodiments 2, 4, 6 and Comparative Embodiments 1-3 according to the invention.

The technical solutions in the embodiments of the invention will be clearly and completely described hereinafter with reference to the accompanying drawings in the embodiments of the invention. Obviously, the described embodiments are only a part of the embodiments of the invention, and not all of them. Based on the embodiments of the invention, all other embodiments obtained by those of ordinary skill in the art without creative efforts shall fall within the protection scope of the invention.

Unless otherwise defined, all technical and scientific terms used herein have the same meaning as commonly understood by one of ordinary skill in the art to which this invention belongs. In addition, any methods and materials similar or equivalent to those described can be used in the invention. The preferred embodiments and materials described herein are exemplary only and are not intended to limit the scope of the application.

In the following embodiments, unless otherwise specified, conventional methods are used; the materials used in the following embodiments, unless otherwise specified, are newly purchased materials from the market; the parts mentioned are all parts by weight. Among them: the isotopic purity of acrylamide-$^{13}C_3$ used is ≥99%; the TPGDA used has a polyethylene glycol chain with n=3, free acrylic acid content <500 ppm, and color <50; the HAMA used has a substitution degree of 1.2 and an HA base molecular weight (MW) of 100 kDa; the antifreeze protein used is derived from *Polygonum viviparum* leaves; the enzyme activity of the β-mannanase used is ≥50,000 U/g; the pH 4.0 citrate buffer solution is prepared from citric acid, sodium citrate, and distilled water at a concentration of 0.1 M; the CaCl₂ used is in dihydrate form.

In the following embodiments and comparative embodiments, the photo-curing process refers to curing under 365 nm wavelength, 25 mW/cm$^2$ UV light irradiation for 60 seconds.

In the following embodiments and comparative embodiments, the cooling matrix comprises the following raw materials in parts by weight: 60 parts of antifreeze protein, 4 parts of menthyl amide, 90 parts of konjac glucomannan, 18.8 parts of hinokitiol, 1.2 parts of NHS, 2 parts of CaCl$_2$, and 0.6 parts of β-mannanase. The preparation method of the cooling matrix is as follows:

S1: weighing 90 parts of konjac glucomannan and dissolving it in 120 parts of deionized water, adding 0.6 parts of activated β-mannanase and reacting for 30 minutes, deactivating the enzyme at 90° C. for 15 minutes, then adding 18.8 parts of hinokitiol and 1.2 parts of NHS, reacting at 50° C. under nitrogen atmosphere for 3 hours, dialyzing using a 500 Da dialysis bag for 1 hour, to obtain a grafted solution;

S2: weighing 60 parts of antifreeze protein and dissolving it in 104 parts of deionized water to obtain an antifreeze protein solution; weighing 4 parts of menthyl amide and dissolving it in 8 parts of anhydrous ethanol, then adding it to the antifreeze protein solution at 4° C., 80 rpm, and a rate of 2 mL/min while stirring; after complete addition, continuing stirring for 4 hours, to obtain an inclusion solution;

S3: mixing the grafted solution and the inclusion solution uniformly, adding 2 parts of CaCl$_2$, homogenizing at 12,000 rpm for 10 minutes, to obtain the cooling matrix; the average particle size detected was 235.9 nm, with a PDI of 0.183.

Embodiment 1: a self-regulating photo-curable cooling hydrogel, wherein the hydrogel comprises the following raw materials in parts by weight: 10 parts of cooling matrix, 18 parts of acrylamide-$^{13}$C$_3$, 42 parts of glycerol, 5 parts of TPGDA, 0.05 parts of MBA, and 0.1 parts of TPO-L.

The embodiment further provides a preparation method of the self-regulating photo-curable cooling hydrogel, specifically comprising the following steps:

step 1: weighing 18 parts of acrylamide-$^{13}$C$_3$ and dissolving it in 25 parts of deionized water, adding 42 parts of glycerol, and stirring at 400 rpm for 15 minutes, to obtain an aqueous phase with a viscosity of 113.2 mPa s;

step 2: weighing 5 parts of TPGDA and 0.1 parts of TPO-L, mixing them under light-proof conditions, stirring at 200 rpm until clear, to obtain an oil phase; mixing the oil phase and the aqueous phase uniformly, then adding 10 parts of the cooling matrix and 0.05 parts of MBA thereto, to obtain a pre-gel;

step 3: adjusting the pH of the pre-gel to 4.72 using a pH 4.0 citrate buffer, and drying in a 60° C. vacuum drying oven until the water content is 19.4%, to obtain the self-regulating photo-curable cooling hydrogel.

Embodiment 2: a self-regulating photo-curable cooling hydrogel, wherein the hydrogel comprises the following raw materials in parts by weight: 13 parts of cooling matrix, 26 parts of acrylamide-$^{13}$C$_3$, 34 parts of glycerol, 5 parts of TPGDA, 0.1 parts of MBA, and 0.2 parts of TPO-L.

The embodiment further provides a preparation method of the self-regulating photo-curable cooling hydrogel, specifically comprising the following steps:

step 1: weighing 26 parts of acrylamide-$^{13}$C$_3$ and dissolving it in 22 parts of deionized water, adding 34 parts of glycerol, and stirring at 400 rpm for 15 minutes, to obtain an aqueous phase with a viscosity of 134.8 mPa s;

step 2: weighing 5 parts of TPGDA and 0.2 parts of TPO-L, mixing them under light-proof conditions, stirring at 200 rpm until clear, to obtain an oil phase; mixing the oil phase and the aqueous phase uniformly, then adding 13 parts of the cooling matrix and 0.1 parts of MBA thereto, to obtain a pre-gel;

step 3: adjusting the pH of the pre-gel to 4.54 using a pH 4.0 citrate buffer, and drying in a 60° C. vacuum drying oven until the water content is 20.5%, to obtain the self-regulating photo-curable cooling hydrogel.

Embodiment 3: a self-regulating photo-curable cooling hydrogel, wherein the hydrogel comprises the following raw materials in parts by weight: 17 parts of cooling matrix, 33 parts of acrylamide-$^{13}$C$_3$, 27 parts of glycerol, 5 parts of TPGDA, 0.15 parts of PEG400, and 0.3 parts of TPO-L.

The embodiment further provides a preparation method of the self-regulating photo-curable cooling hydrogel, specifically comprising the following steps:

step 1: weighing 33 parts of acrylamide-$^{13}$C$_3$ and dissolving it in 18 parts of deionized water, adding 27 parts of glycerol, and stirring at 400 rpm for 15 minutes, to obtain an aqueous phase with a viscosity of 192.4 mPa s;

step 2: weighing 5 parts of TPGDA and 0.3 parts of TPO-L, mixing them under light-proof conditions, stirring at 200 rpm until clear, to obtain an oil phase; mixing the oil phase and the aqueous phase uniformly, then adding 17 parts of the cooling matrix and 0.15 parts of PEG400 thereto, to obtain a pre-gel;

step 3: adjusting the pH of the pre-gel to 4.54 using a pH 4.0 citrate buffer, and drying in a 60° C. vacuum drying oven until the water content is 19.8%, to obtain the self-regulating photo-curable cooling hydrogel.

Embodiment 4: a self-regulating photo-curable cooling hydrogel, wherein the hydrogel comprises the following raw materials in parts by weight: 10 parts of cooling matrix, 20 parts of acrylamide-$^{13}$C$_3$, 40 parts of glycerol, 5 parts of TPGDA, 0.08 parts of PEG400, and 0.2 parts of Irgacure 2959.

The embodiment further provides a preparation method of the self-regulating photo-curable cooling hydrogel, specifically comprising the following steps:

step 1: weighing 20 parts of acrylamide-$^{13}$C$_3$ and dissolving it in 25 parts of deionized water, adding 40 parts of glycerol, and stirring at 400 rpm for 15 minutes, to obtain an aqueous phase with a viscosity of 120.8 mPa s;

step 2: weighing 5 parts of TPGDA and 0.2 parts of Irgacure 2959, mixing them under light-proof conditions, stirring at 200 rpm until clear, to obtain an oil phase; mixing the oil phase and the aqueous phase uniformly, then adding 10 parts of the cooling matrix and 0.08 parts of PEG400 thereto, to obtain a pre-gel;

step 3: adjusting the pH of the pre-gel to 4.71 using a pH 4.0 citrate buffer, and drying in a 60° C. vacuum drying oven until the water content is 21.4%, to obtain the self-regulating photo-curable cooling hydrogel.

Embodiment 5: a self-regulating photo-curable cooling hydrogel, wherein the hydrogel comprises the following raw materials in parts by weight: 10 parts of cooling matrix, 20 parts of acrylamide-$^{13}$C$_3$, 40 parts of glycerol, 5 parts of TPGDA, 0.08 parts of HAMA, and 0.2 parts of Irgacure 2959.

The embodiment further provides a preparation method of the self-regulating photo-curable cooling hydrogel, specifically comprising the following steps:

step 1: weighing 20 parts of acrylamide-$^{13}C_3$ and dissolving it in 25 parts of deionized water, adding 40 parts of glycerol, and stirring at 400 rpm for 15 minutes, to obtain an aqueous phase with a viscosity of 127.2 mPa s;

step 2: weighing 5 parts of TPGDA and 0.2 parts of Irgacure 2959, mixing them under light-proof conditions, stirring at 200 rpm until clear, to obtain an oil phase; mixing the oil phase and the aqueous phase uniformly, then adding 10 parts of the cooling matrix and 0.08 parts of HAMA thereto, to obtain a pre-gel;

step 3: adjusting the pH of the pre-gel to 4.66 using a pH 4.0 citrate buffer, and drying in a 60° C. vacuum drying oven until the water content is 20.2%, to obtain the self-regulating photo-curable cooling hydrogel.

Embodiment 6: a self-regulating photo-curable cooling hydrogel, wherein the hydrogel comprises the following raw materials in parts by weight: 15 parts of cooling matrix, 25 parts of acrylamide-$^{13}C_3$, 35 parts of glycerol, 5 parts of TPGDA, 0.08 parts of HAMA, and 0.2 parts of Irgacure 2959.

The embodiment further provides a preparation method of the self-regulating photo-curable cooling hydrogel, specifically comprising the following steps:

step 1: weighing 25 parts of acrylamide-$^{13}C_3$ and dissolving it in 20 parts of deionized water, adding 35 parts of glycerol, and stirring at 400 rpm for 15 minutes, to obtain an aqueous phase with a viscosity of 144.8 mPa s;

step 2: weighing 5 parts of TPGDA and 0.2 parts of Irgacure 2959, mixing them under light-proof conditions, stirring at 200 rpm until clear, to obtain an oil phase; mixing the oil phase and the aqueous phase uniformly, then adding 10 parts of the cooling matrix and 0.08 parts of HAMA thereto, to obtain a pre-gel;

step 3: adjusting the pH of the pre-gel to 4.81 using a pH 4.0 citrate buffer, and drying in a 60° C. vacuum drying oven until the water content is 19.9%, to obtain the self-regulating photo-curable cooling hydrogel.

Embodiment 7: an application of the hydrogel in cooling gel dressings.

Based on the material formulation and preparation method in Embodiment 4, prepare the cooling hydrogel. Using the adsorption mold production method: take a cleaned and dried mold, inject the prepared cooling hydrogel into it, then cover it with a backing layer. Cure under ultraviolet light irradiation at 365 nm wavelength and 25 mW/cm² intensity for 60 seconds, followed by compression molding to obtain the cooling gel pad. The contact surface between the backing layer and the hydrogel contains an adhesive layer.

Embodiment 8: an application of the hydrogel in in-situ injectable gels.

Based on the material formulation and preparation method in Embodiment 2, prepare the cooling hydrogel. Inject the prepared cooling hydrogel into the lesion site of subcutaneous tumor-bearing model mice. Perform in-situ photo-curing under 365 nm wavelength and 25 mW/cm² intensity for 60 seconds to achieve shaping. Utilize the acrylamide-$^{13}C_3$ isotope within the cooling hydrogel for metabolic tracing.

Embodiment 9: an application of the hydrogel in drug-loaded gel dressings.

Weigh 0.64 parts of Mupirocin and disperse it in 1.36 parts of ethanol to obtain a drug solution. Uniformly mix and homogenize the drug solution, 0.04 parts of Tween 80, and 30 parts of the cooling hydrogel prepared according to Embodiment 3 to obtain a drug-loaded gel. Uniformly coat the drug-loaded gel onto a mold containing a dressing backing liner. Cure under ultraviolet light irradiation at 365 nm wavelength and 25 mW/cm² intensity for 60 seconds, followed by compression molding, to obtain the drug-loaded gel dressing.

Comparative Embodiment 1: differs from Embodiment 2 in that glycerol is replaced with an equal mass of deionized water for hydrogel preparation. All other aspects are identical to Embodiment 1.

Comparative Embodiment 2: differs from Embodiment 2 in that the cooling matrix is not prepared; an equal mass and concentration solution of menthyl amide is used for hydrogel preparation instead.

Comparative Embodiment 3 is a 30% acrylamide hydrogel containing 3 mg/mL menthol.

Investigation of Thermosensitivity Threshold

Using a DHR-3 rheometer connected to a temperature control system, perform a temperature sweep to examine the changes in rheological properties of the hydrogels prepared in Embodiments 1-6 and Comparative Embodiments 1-3 with temperature. Temperature sweep parameters: 25-40° C., heating rate 2° C./min. Measure the point of sudden drop in the storage modulus G. Record the temperature point where G decreases by 10% and calculate $\Delta G$ (the difference in G between 25° C. and 32° C.). Results are shown in Table 1.

Investigation of Cooling Effect

After photo-curing the cooling hydrogels prepared in Embodiments 2, 4, 6 and Comparative Embodiments 1-3, adjust their initial temperature to 20° C. Place them on the same constant temperature pad maintained at 40° C. for incubation. Use temperature sensors to record the initial hydrogel temperature and the temperatures after incubating for 5 minutes, 10 minutes, 30 minutes, 1 hour, 2 hours, and 4 hours. Results are shown in FIG. 1.

Investigation of Mechanical Properties and Injectability

Figure 2:
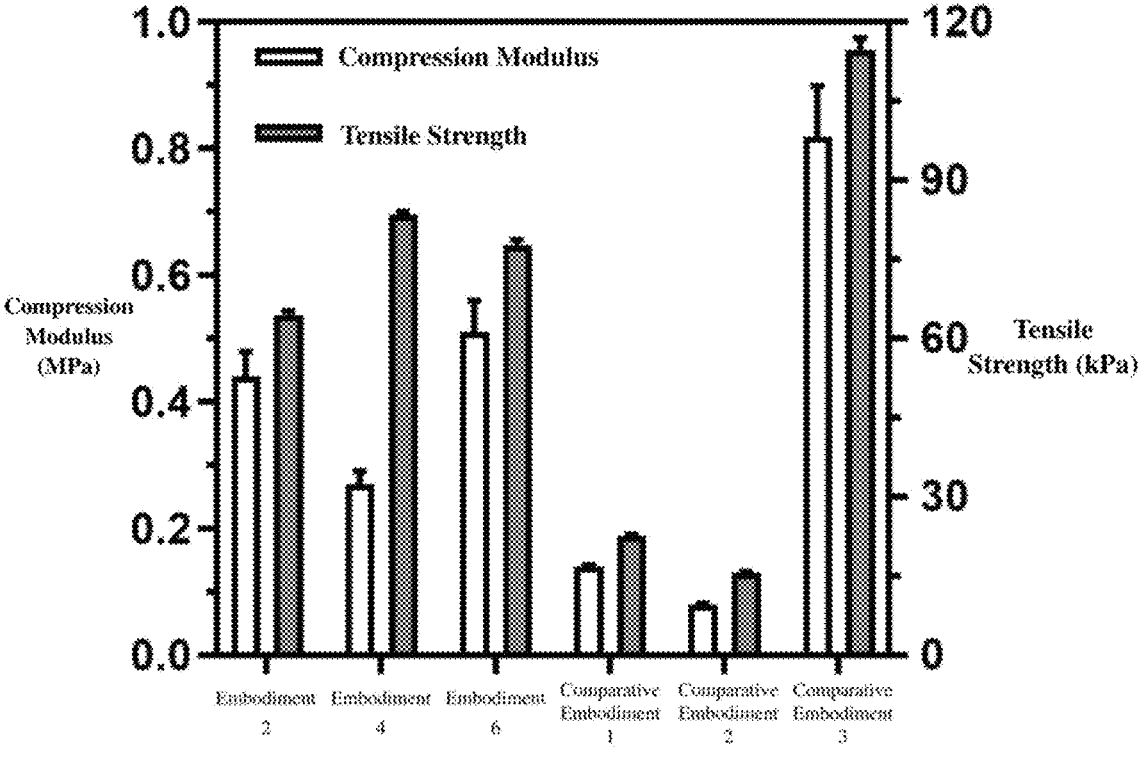
FIG. 2 shows the mechanical property test results of the cooling hydrogels after photo-curing prepared in Embodiments 2, 4, 6 and Comparative Embodiments 1-3 according to the invention.
Figure 3:
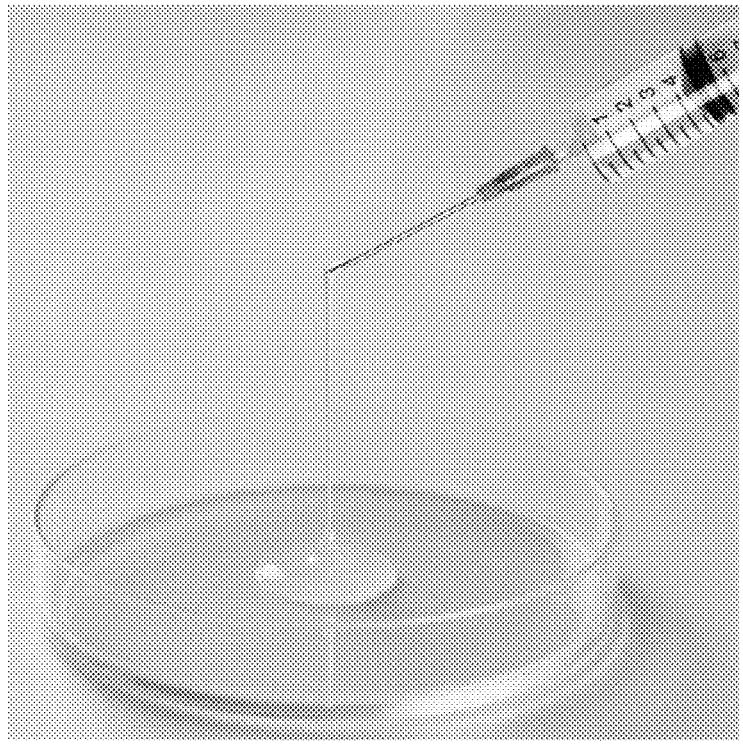
FIG. 3 shows an injectability investigation of the cooling hydrogel prepared in Embodiment 2 according to the invention.

Using a texture analyzer, measure the compression modulus and tensile strength of the photo-cured cooling hydrogels prepared in Embodiments 2, 4, 6 and Comparative Embodiments 1-3. Results are shown in FIG. 2. Draw the cooling hydrogel prepared in Embodiment 2 into a 10 mL syringe to investigate its injectability. Results are shown in FIG. 3.

Observation of Microscopic Morphology

Figure 4:
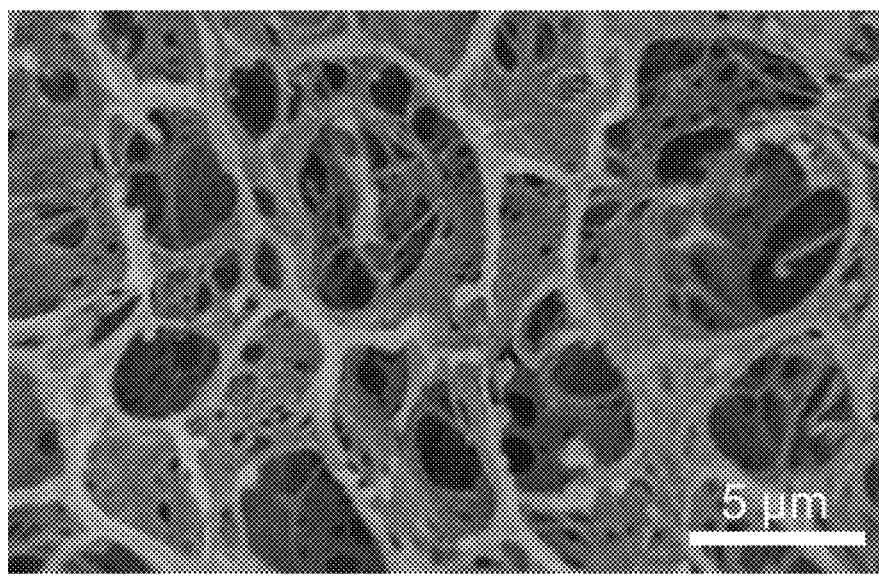
FIG. 4 shows the scanning electron microscopy characterization results of the cooling hydrogel after photo-curing prepared in Embodiment 4 according to the invention.

Fix the photo-cured cooling hydrogel prepared in Embodiment 4 onto a sample holder using conductive adhesive. Apply a gold coating using a sputter coater. Examine the morphology of the self-regulating photo-curable cooling hydrogel using a scanning electron microscope. Results are shown in FIG. 4.

Application of the Dressing

Figure 5:
FIG. 5 is an appearance diagram of the cooling gel dressing prepared in Embodiment 7 according to the invention.

Examine and document the appearance of the cooling gel dressing prepared in Embodiment 7. Results are shown in FIG. 5.

9

TABLE 1

| Investigation of Thermosensitivity | | | |
|---|---|---|---|
| Groups | Response Threshold (° C.) | ΔG (×10⁴ Pa) | Hysteresis Quality (° C.) |
| Embodiment 1 | 32.3 ± 0.3 | 1.2 | 1.5 |
| Embodiment 2 | 31.9 ± 0.1 | 2.8 | 0.3 |
| Embodiment 3 | 28.4 ± 0.4 | 1.5 | 1.8 |
| Embodiment 4 | 30.3 ± 0.4 | 1.8 | 0.8 |
| Embodiment 5 | 34.5 ± 0.5 | 2.1 | 0.5 |
| Embodiment 6 | 32.2 ± 0.3 | 2.3 | 0.6 |
| Comparative Embodiment 1 | 35.2 ± 0.6 | 0.3 | 3.2 |
| Comparative Embodiment 2 | N/A | N/A | N/A |
| Comparative Embodiment 3 | N/A | <0.05 | N/A |

Results from Table 1 show that the photo-cured hydrogels prepared in Embodiments 1-6 and Comparative Embodiment 1 all possess a certain temperature response threshold. Among them, the hydrogels prepared in Embodiments 3 and 4 have the lowest temperature thresholds. In contrast, the hydrogels prepared in Comparative Embodiments 2 and 3 exhibit no temperature responsiveness and no measurable storage modulus, therefore they are unable to buffer temperature increases.

Results from FIG. 1 (Temperature-Time Change Curves) show that compared to the hydrogels prepared in Comparative Embodiments 1-3, the photo-cured hydrogels prepared in Embodiments 2, 4, and 6 heat up more slowly within the first 30 minutes. After 30 minutes, their temperature remains stable within a threshold plateau period for approximately 1.5 hours, and then continues to rise after about 2 hours. This fully demonstrates the importance of adding the cooling matrix to the hydrogel for achieving the cooling effect.

Results from FIG. 2 (Hydrogel Mechanical Properties) show that after photo-curing, the compression modulus and tensile strength of the hydrogels prepared in Embodiments 2, 4, and 6 are significantly higher than those of all Comparative Embodiment groups. Among them, Embodiments 4 and 6 exhibit superior mechanical properties, indicating certain structural stability and mechanical strength.

Results from FIG. 3 (Gel Injectability Experiment) show that the cooling hydrogel prepared in Embodiment 2 possesses injectability. It can be used for injection into tissues such as tumors, bones, and organs, followed by in-situ curing, enabling in vivo metabolic tracing and ex vivo dressing formation.

Results from FIG. 4 (Scanning Electron Microscopy) show that the photo-cured cooling hydrogel prepared in Embodiment 4 possesses a relatively large gel skeleton, which is beneficial for enhancing mechanical properties. Furthermore, the larger skeleton and smaller gel pores facilitate the slow release of the cooling matrix, achieving a long-lasting temperature control effect.

The appearance image of the cooling gel dressing in FIG. 5 demonstrates good curing and molding properties and suitability for topical application.

Although embodiments of the invention have been shown and described hereinabove, it will be understood by those of ordinary skill in the art that various changes, modifications, substitutions, and alterations may be made to these embodiments without departing from the principles and spirit of the invention. The scope of the invention is defined by the appended claims and the equivalents thereof.

The invention and the embodiments thereof are described hereinabove, and this description is not restrictive. What is shown in the drawings is only one of the embodiments of the invention, and the actual structure is not limited thereto. All in all, structural methods and embodiments similar to the technical solution without deviating from the purpose of the invention made by those of ordinary skill in the art without creative design shall all fall within the protection scope of the invention.

The invention claimed is:

1. A self-regulating photo-curable cooling hydrogel, wherein the hydrogel comprises the following raw materials in parts by weight: 10-17 parts of cooling matrix, 18-33 parts of acrylamide-$^{13}$C$_3$, 27-42 parts of glycerol, 5 parts of TPGDA (tripropylene glycol diacrylate), 0.05-0.15 parts of crosslinking agent, and 0.1-0.3 parts of photoinitiator;

the cooling matrix comprises the following raw materials: antifreeze protein, menthyl amide, konjac glucomannan, hinokitiol, NHS (N-hydroxysuccinimide), CaCl$_2$), and β-mannanase; the preparation method of the cooling matrix comprises the following steps:

S1: dissolving konjac glucomannan, then adding β-mannanase, hinokitiol, and NHS to obtain a grafted solution;

S2: dissolving antifreeze protein to obtain an antifreeze protein solution; dissolving menthyl amide and adding it to the antifreeze protein solution to obtain an inclusion solution;

S3: mixing the grafted solution, the inclusion solution, and CaCl$_2$), followed by homogenization, to obtain the cooling matrix.

2. The self-regulating photo-curable cooling hydrogel of claim 1, wherein the mass ratio of the antifreeze protein, menthyl amide, konjac glucomannan, hinokitiol, NHS, CaCl$_2$), and β-mannanase is 15:1:22.5:4.7:0.3:0.5:0.15.

3. The self-regulating photo-curable cooling hydrogel of claim 1, wherein the crosslinking agent is selected from any one of MBA (N,N'-methylenebisacrylamide), PEG400 (polyethylene glycol 400), and HAMA (methacrylated hyaluronic acid); the photoinitiator is selected from any one of TPO-L (ethyl(2,4,6-trimethylbenzoyl)phenylphosphinate) and (2-hydroxy-4'-(2-hydroxyethoxy)-2-methylpropiophenone).

4. A preparation method of the self-regulating photo-curable cooling hydrogel of claim 1, wherein the specific preparation method is as follows:

step 1: dissolving acrylamide-$^{13}$C3, adding glycerol, to obtain an aqueous phase;

step 2: mixing TPGDA and the photoinitiator to obtain an oil phase; mixing the oil phase and the aqueous phase uniformly, then adding the cooling matrix and the crosslinking agent thereto, to obtain a pre-gel; and step 3: adjusting the pH of the pre-gel and drying it, to obtain the self-regulating photo-curable cooling hydrogel.

5. An application method of using a self-regulating photo-curable cooling hydrogel, wherein the hydrogel comprises the following raw materials in parts by weight: 10-17 parts of cooling matrix, 18-33 parts of acrylamide-13C3, 27-42 parts of glycerol, 5 parts of TPGDA (tripropylene glycol diacrylate), 0.05-0.15 parts of crosslinking agent, and 0.1-0.3 parts of photo initiator;

wherein the cooling matrix comprises the following raw materials: antifreeze protein, menthyl amide, konjac glucomannan, hinokitiol, NHS (N-hydroxysuccinimide), CaCl2), and β-mannanase;

wherein the preparation method of the cooling matrix comprises the following steps:

S1: dissolving konjac glucomannan, then adding β-mannanase, hinokitiol, and NHS to obtain a grafted solution;

S2: dissolving antifreeze protein to obtain an antifreeze protein solution; dissolving menthyl amide and adding it to the antifreeze protein solution to obtain an inclusion solution; and S3: mixing the grafted solution, the inclusion solution, and CaCl2), followed by homogenization, to obtain the cooling matrix; and wherein the method of using the self-regulating photo-curable cooling hydrogel comprises: preparing the hydrogel into a form selected from the group consisting of: drug-loaded gel dressings, cooling gel pads, cooling gel dressing bags, cooling gel injection products, and in-situ injectable gels.

6. The application method of using the self-regulating photo-curable cooling hydrogel of claim 5, wherein preparing the cooling gel pad is as follows:

placing the cooling hydrogel in an adsorption mold, and performing UV light curing and compression molding, to obtain the cooling gel pad.

7. The application method of using the self-regulating photo-curable cooling hydrogel of claim 5, wherein the drug-loaded gel dressing comprises the following raw materials: a drug, Tween 80, and the cooling hydrogel; and wherein preparing the drug-loaded gel dressing is as follows:

dispersing the drug to obtain a drug solution;

uniformly mixing the drug solution, Tween 80, and the cooling hydrogel, then performing UV light curing and compression molding in a mold, to obtain the drug-loaded gel dressing.

8. The application of the self-regulating photo-curable cooling hydrogel of claim 7, wherein the UV light curing process is performed at a wavelength of 365 nm and a light intensity of 25 mW/cm$^2$.

\* \* \* \* \*